United States Patent [19]
Towsley

[11] Patent Number: 5,669,873
[45] Date of Patent: Sep. 23, 1997

[54] FLEXIBLE KNEE AND LEG BRACE

[76] Inventor: Harold E. Towsley, 1821 Greenstone Dr., New Haven, Fort Wayne, Ind. 46774

[21] Appl. No.: 519,082

[22] Filed: Aug. 24, 1995

[51] Int. Cl.⁶ ........................................... A61F 5/00
[52] U.S. Cl. .................... 602/26; 602/23; 602/16
[58] Field of Search ......................... 602/5, 16, 23–26

[56] References Cited

U.S. PATENT DOCUMENTS

| | | | |
|---|---|---|---|
| 1,313,181 | 8/1919 | Grundmann | 602/26 |
| 1,375,507 | 4/1921 | Grundmann | 602/26 |
| 4,130,115 | 12/1978 | Taylor | 602/26 X |
| 4,245,629 | 1/1981 | Cummins | 602/26 X |
| 4,573,455 | 3/1986 | Hoy | 602/16 |
| 4,726,362 | 2/1988 | Nelson | 602/16 X |
| 4,969,452 | 11/1990 | Petrofsky et al. | 602/26 X |
| 5,020,790 | 6/1991 | Beard et al. | 602/16 |
| 5,121,742 | 6/1992 | Engen | 602/26 X |
| 5,456,659 | 10/1995 | Gildersleeve et al. | 602/26 X |

Primary Examiner—Linda C. Dvorak
Attorney, Agent, or Firm—Roger M. Rickert

[57] ABSTRACT

An orthopedic brace is formed from at least two relatively rigid hollowed-out parallelepiped portions joined along a relatively thin web of flexible material common to the two portions to provide pivotal motion between the two portions. Relative pivotal movement between the two portions is selectively restricted by an elongated threaded rod which is pivotably affixed at one end to one of the parallelepiped portions and extends through a portion of the other parallelepiped portion with a nut threadedly engaging the rod for adjustment therealong to selectively pull the other parallelepiped portion angularly toward the one parallelepiped portion. The number of such portions joined together is somewhat arbitrary. In the preferred knee brace form, there are four parallelepiped portions each joined to another to form a pair by a relatively thin web and each pair having a threaded rod and nut for selectively restricting pivotal movement between the portions of the pair. The pairs are similarly joined to a hinge arrangement allowing normal knee motion. The normal knee motion may be restricted if desired.

23 Claims, 2 Drawing Sheets

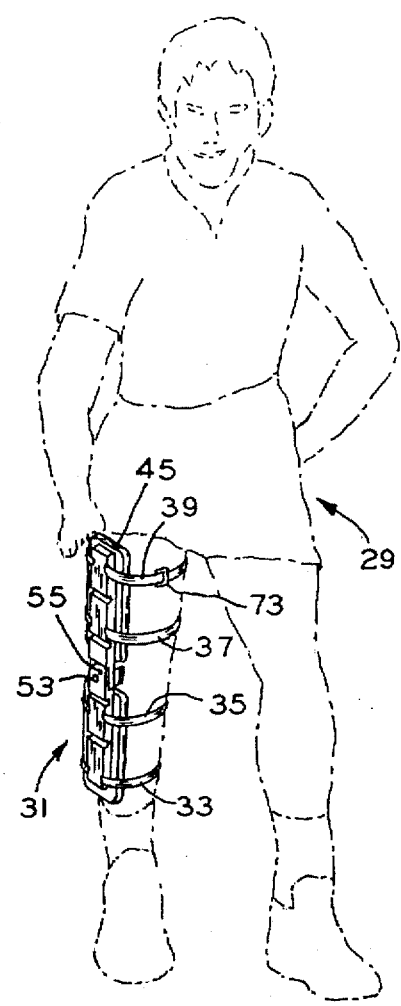
FIG_1
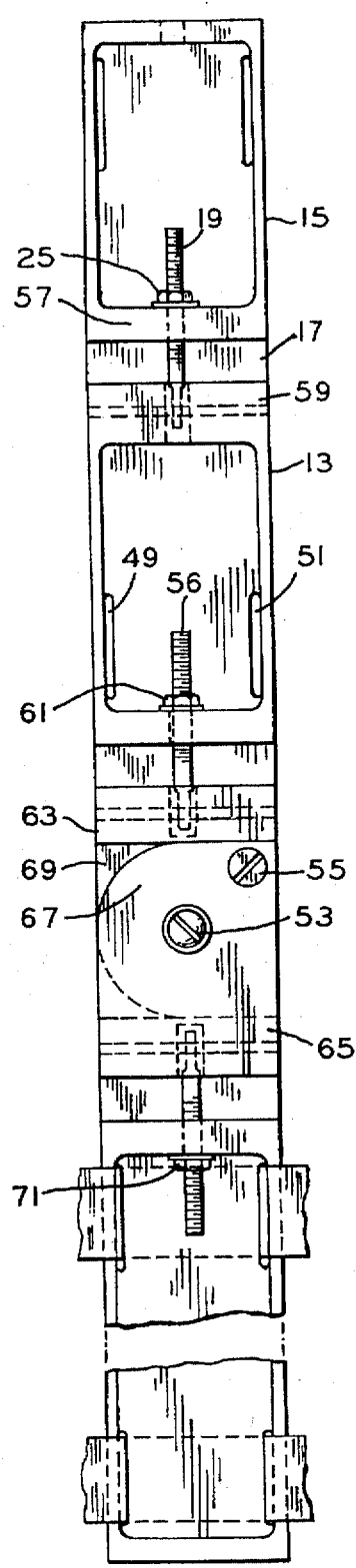
FIG_3
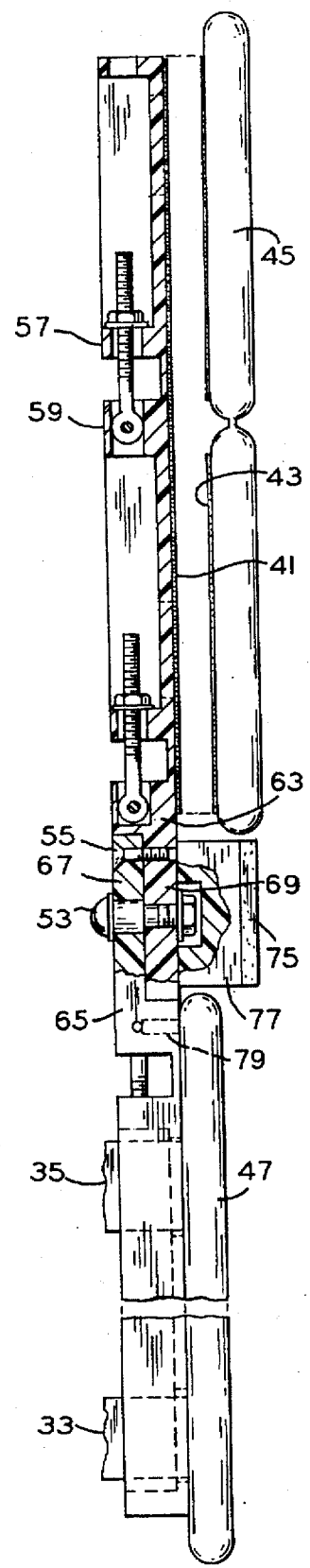
FIG_2

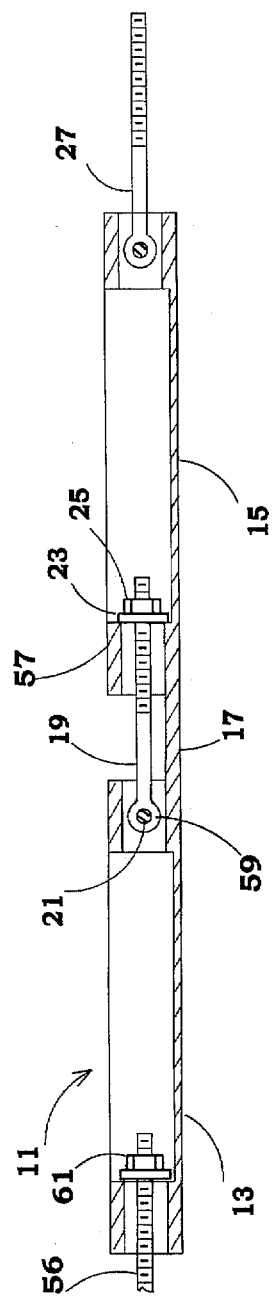
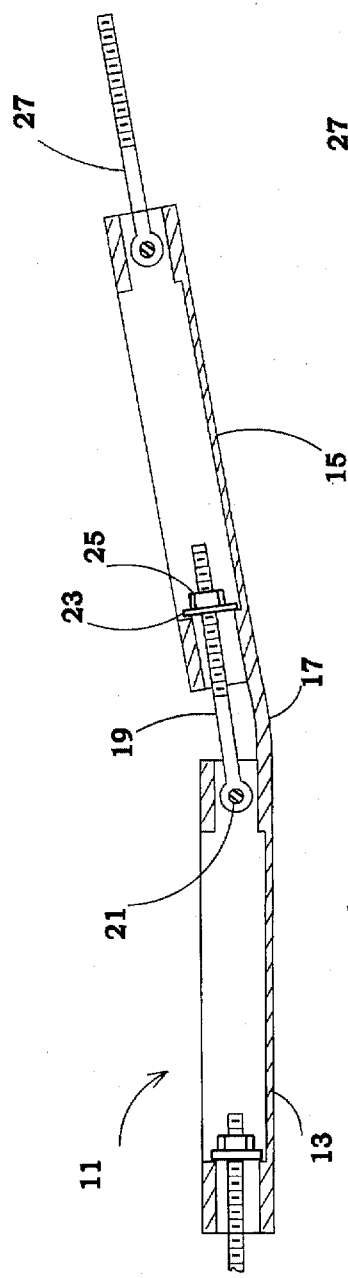
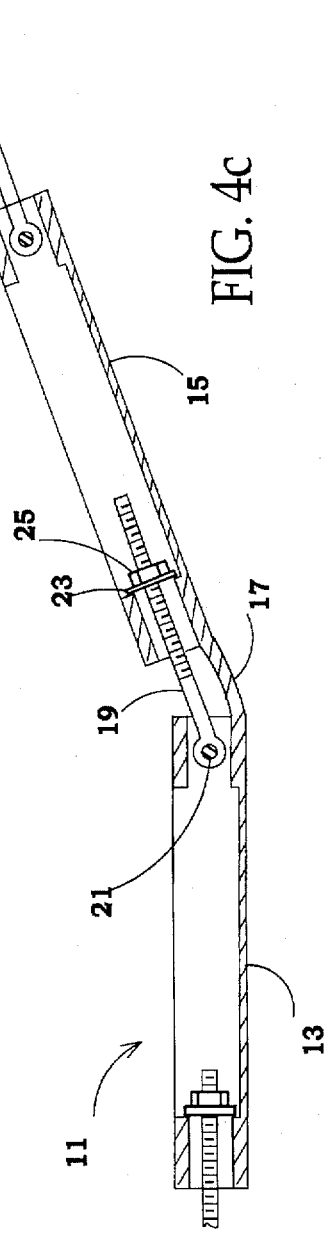
FIG. 4a
FIG. 4b
FIG. 4c 5,669,873

1

FLEXIBLE KNEE AND LEG BRACE

BACKGROUND OF THE INVENTION

The present invention relates generally to orthotic devices of the type employed to arrest or correct deformation of a body part.

Such orthotic devices are generally quite complex, yet limited in their range of adjustments and hence quite individualized in their applicability. These problems are exaggerated when the orthosis is adapted to a highly articulated body part such as a leg, arm, or finger.

Among the several objects of the present invention may be noted the provision of a highly individualizable orthopedic brace; the provision of an externally applied (non-invasive) body appliance which may be easily and repeatedly modified to urge certain body parts in selected directions and by selected amounts relative to other body parts; and the provision of a unique knee brace. These as well as other objects and advantageous features of the present invention will be in part apparent and in part pointed out hereinafter.

In general, an externally applied non-invasive body orthopedic appliance includes a plurality of rigid members certain pairs of which are pivotably coupled together for relative angular movement about an axis. There are arrangements for selectively restricting the angular movement of the pivotably coupled rigid members and there are at least two straps, one removably attached to each rigid member, for encircling portions of a body to secure the rigid members to the body. Each strap has a coupling arrangement for adjustably joining its free ends. A pair of resilient pads, one removably affixed to each of the rigid members are interposed between the rigid member and a corresponding body portion.

Also in general and in one form of the invention, an orthopedic appliance for application to a leg of a human being spanning the knee joint is formed from two elongated relatively rigid sections joined at respective first ends for relative pivotal motion about an axis which is collinear with the axis of motion of the leg knee joint. Two straps are fastened to one section and adapted to encircle the leg thigh and two straps are fastened to the other section and adapted to encircle the lower leg portion. Each segment may be selectively deformed to apply a bending moment to the leg.

BRIEF DESCRIPTION OF THE DRAWING

FIG. 1 is a perspective view of the brace of the present invention applied to a human leg;

FIG. 2 is a front elevation view partly in cross-section of the leg brace of FIG. 1;

FIG. 3 is a side elevation view from the left side of FIG. 2; and

FIGS. 4a–4c are cross-sectional representations of an illustrative pair of articulated segments experiencing sequentially increasing angular displacement.

Corresponding reference characters indicate corresponding parts throughout the several views of the drawing.

The exemplifications set out herein illustrate a preferred embodiment of the invention in one form thereof and such exemplifications are not to be construed as limiting the scope of the disclosure or the scope of the invention in any manner.

DESCRIPTION OF THE PREFERRED EMBODIMENT

In FIG. 1, the right leg of a wearer 29 has an orthopedic brace 31 fastened thereto by straps 33, 35, 37 and 39 which

2 are passed through slots such as 49 and 51 (FIG. 3) and encircle the wearer's leg. Mating strips of VELCRO 41 and 43 (FIG. 2) allow a pair of resilient pads 45 and 47 to be removably affixed to the brace portions and to be interposed between the brace and a corresponding portion of the body such as the leg. A pin or screw 53 provides a pivot axis for the brace which is collinear with the knee pivot axis, or flexion axis allowing free knee movement while restricting any lateral leg movement. An optional screw 55 may be passed through both halves of the hinge arrangement to immobilize the knee joint. A knee pressure block 77 and foam rubber pad 75 are located adjacent the screw 53 and are adapted to provide lateral pressure against a wearer's knee.

The basic components of the brace are rigid members, also called hollowed-out parallelepiped portions or segments. A two segment assembly 11 including rigid members such as 13 and 15 is shown in FIGS. 4a–4c. These members comprise hollowed-out rectangular parallelepipeds joined to an adjacent rigid member along adjacent generally parallel edges by a relatively thin web 17 of flexible material which is common to the two portions 13 and 15 to provide relative pivotal motion between the two portions as shown successively in FIGS. 4a, 4b and 4c. The angular relationship between adjacent segments is selectively restricted by an elongated threaded rod 19 which has an eye 59 which is pivotably affixed at one end to a transverse pin 21 of the rigid member 13 and extends through an endwall portion 57 of the other rigid member 15. Pin 21 may be held in position by a set screw 79 or otherwise as desired. There is a washer 23 and a nut 25 threadedly engaging the rod 19. The nut is helically movable along the rod to selectively pull the rigid members angularly toward one another. The pin 21 extends generally parallel to the axis of relative angular movement between the two members. The brace segments 13 and 15 normally assume the shape shown in FIG. 4a. When the nut 25 is tightened, the segments are drawn angularly toward one another against the natural resilience of the web 17. Note that the nut 25 is successively closer to the eye 59 as the two segments are pulled from their natural collinear relationship of FIG. 4a. While only two segments 13 and 15 are shown in FIGS. 4a–4c, it will be understood that the number of segments is somewhat arbitrary. Rod 27 is shown for angularly fixing the relationship between segment 15 and another segment, not shown. Similarly, the rod 56 and nut 61 are shown for angularly fixing the relationship between segment 13 and another segment 63 of FIGS. 2 and 3.

Returning to FIGS. 2 and 3, the end segments 63 and 65 differ from those shown in FIGS. 4a–4c and include coplanar overlapping end portions 69 and 67 which are pivotably coupled together for movement through about ninety degrees by the hinge pin 53. This pin 53 defines a pivotal axis between segments 63 and 65 which is orthogonal (perpendicular in the vector sense) to the axes of pins such as 59. As noted earlier, the angular movement about pin 53 may be restricted by a screw 55 passing through one overlapping end portion 67 and into end portion 69. selectively restricting the angular movement of the third and said one rigid members.

As an example, assume the wearer 29 suffers from genu varum, a condition commonly known as being "bowlegged." The brace may be utilized to apply a corrective medial pressure. Once the straps 33, 35, 37 and 39 have been coupled or tightened as by buckles such as 73, VELCRO strips or the like, and the pivot axis of pin 53 is aligned with wearer 29's knee joint, nuts 25, 61 and 71 are threaded toward the eyes such as 59. This causes the brace to bend concave outwardly urging the central portion of the brace against the wearer's knee while exerting a tension primarily on the outer straps 33 and 39 and applying a bending moment to the leg in a direction tending to correct the bowlegged condition. While described as an orthopedic device, the brace may be used simply to immobilize a body part, for example, subsequent to an injury. The techniques of the present invention may be used to apply almost any desired pressure to virtually any body part. A knock-kneed (genu valgum) condition could be similarly treated by reversing the bending moment applied, for example, by reversing the brace end-for-end and attaching the brace to the medial side of the leg. Other examples include treatment of a knee joint with a loose prothesis or a knee joint which suffers from deterioration of the surfaces. Numerous other brace configurations as well as numerous other applications should now be apparent.

From the foregoing, it is now apparent that a novel orthosis has been disclosed meeting the objects and advantageous features set out hereinbefore as well as others, and that numerous modifications as to the precise shapes, configurations and details may be made by those having ordinary skill in the art without departing from the spirit of the invention or the scope thereof as set out by the claims which follow.

What is claimed is:

1. An externally applied non-invasive body appliance adapted to span a body joint comprising:

at least two rigid members;

means pivotable coupling the two rigid members for relative angular movement about a bending moment axis;

means for selectively restricting the angular movement of the two rigid members about the bending moment axis including means engaging each of the two rigid members for pulling the two rigid members angularly toward one another; and strap means for encircling portions of a body to secure the rigid members to the body and to transfer bending moment forces to the body joint.

2. The appliance of claim 1 wherein the strap means comprises at least two straps, one removably attached to each rigid member, and each having coupling means for adjustably joining the free ends thereof.

3. The appliance of claim 1 further comprising a pair of resilient pads, one removably affixed to each of the rigid members to be interposed between the rigid member and a corresponding body portion.

4. The appliance of claim 1 further including a third rigid member, means pivotably coupling the third rigid member to one of said two rigid members for relative angular movement about another axis, and means for selectively restricting the angular movement of the third and said one rigid members.

5. The appliance of claim 4 wherein said another axis is a flexion axis and wherein said bending moment axis and said flexion axis are generally orthogonal to one another.

6. The appliance of claim 5 wherein said third rigid member and said one rigid member include coplanar overlapping end portions and the means pivotably coupling the third rigid member and said one rigid member comprises a hinge pin passing orthogonally through the coplanar overlapping end portions.

7. The appliance of claim 4 wherein said another axis is a second bending moment axis and wherein said bending moment axis and said second bending moment axis are generally parallel to one another.

8. The appliance of claim 1 wherein the means for selectively restricting includes a threaded fastener passing through one of the overlapping end portions and at least part way through the other of the overlapping end portions.

9. The appliance of claim 1 wherein the means pivotably coupling comprises a relatively thin elongated web of flexible material common to the two rigid members.

10. The appliance of claim 9 wherein the rigid members comprise hollowed-out rectangular parallelepipeds joined to an adjacent rigid member along adjacent generally parallel edges.

11. The appliance of claim 1 wherein the means for selectively restricting includes an elongated threaded rod pivotably affixed at one end to one of the rigid members and extending through a portion of the other rigid member, and a nut threadedly engaging the rod and helically movable therealong to selectively pull the other member angularly toward the one rigid member.

12. The appliance of claim 11 wherein the rod has an eye near said one end and further comprising a pin passing through the eye and through a portion of said one rigid member generally parallel to said axis.

13. An orthopedic brace including at least two hollowed-out parallelepiped portions joined along a bending moment axis comprising a relatively thin web of flexible material common to the two portions to provide relative pivotal motion between the two portions, and means for selectively restricting relative pivotal movement between the two portions including means engaging each of the two portions for pulling the two portions angularly about the bending moment axis toward one another.

14. The orthopedic brace of claim 13 wherein the means for selectively restricting includes an elongated threaded rod pivotably affixed at one end to one of the parallelepiped portions and extending through a portion of the other parallelepiped portion, and a nut threadedly engaging the rod and helically movable therealong to selectively pull the other parallelepiped portion angularly toward the one parallelepiped portion.

15. The orthopedic brace of claim 14 wherein there are four parallelepiped portions each joined to another to form a pair by a relatively thin web and each pair having a threaded rod and nut for selectively restricting pivotal movement between the portions of the pair.

16. The orthopedic brace of claim 15 wherein one parallelepiped portion of each pair includes an end portion having a planar surface, and the pairs of parallelepiped portions are pivotably joined together by a hinge pin passing through overlapping planar end portions.

17. The orthopedic brace of claim 16 wherein the axes of pivotal motion between individual ones of the pairs are parallel and the axis of pivotal motion between the pairs is perpendicular to the axes of pivotal motion between individual ones of the pairs.

18. The orthopedic brace of claim 17 wherein the brace is adapted to span a body joint, the brace further comprising a plurality of straps, one removably attached to each parallelepiped portion, and each having coupling means for adjustably joining the free ends thereof, the straps adapted to encircling portions of a body to secure the parallelepiped portions to the body and to transfer bending moment forces to the body joint.

19. The orthopedic brace of claim 18 further comprising a pair of resilient pads, one removably affixed to each of the parallelepiped pairs to be interposed between the parallelepiped pairs and a corresponding body portion.

20. The orthopedic brace of claim 19 for application to a leg of a human being spanning the knee joint thereof, two straps adapted to encircle the leg thigh and two straps adapted to encircle the lower leg portion with the axis of pivotal motion between the pairs being collinear with the axis of motion of the leg knee joint.

21. An orthopedic appliance having at least four articulated segments, a first pair of segments pivotably joined for relative angular movement about a first bending moment axis, a second pair of segments pivotably joined for relative angular movement about a second bending moment axis generally parallel to said first bending moment axis, and one of each pair pivotably joined together for angular movement about a third flexion axis generally orthogonal to the first and second bending moment axes, each pair of segments having means for selectively restricting relative pivotal movement between the two pair segments.

22. The orthopedic appliance of claim 21 for application to a leg of a human being spanning the knee joint thereof and further comprising two straps adapted to encircle the leg thigh, two straps adapted to encircle the lower leg portion with the third bending moment axis collinear with the axis of flexion motion of the leg knee joint.

23. An orthopedic appliance for application to a leg of a human being spanning the knee joint thereof and comprising two elongated relatively rigid sections joined at respective first ends for relative pivotal motion about an axis, two straps fastened to one section and adapted to encircle the leg thigh, two straps fastened to the other section and adapted to encircle the lower leg portion with the axis of pivotal motion between the sections being collinear with the axis of motion of the leg knee joint, and means associated with each segment for selectively deforming the associated segment to thereby apply a bending moment to the leg.

* * * * *